United States Patent
Proksch et al.

(10) Patent No.: US 12,165,317 B2
(45) Date of Patent: Dec. 10, 2024

(54) COMPOSITE MEDICAL IMAGING SYSTEMS AND METHODS

(71) Applicant: Intuitive Surgical Operations, Inc., Sunnyvale, CA (US)

(72) Inventors: Daniel Proksch, San Jose, CA (US); Mahdi Azizian, San Jose, CA (US); A. Jonathan McLeod, Sunnyvale, CA (US); Pourya Shirazian, Menlo Park, CA (US)

(73) Assignee: Intuitive Surgical Operations, Inc., Sunnyvale, CA (US)

( * ) Notice: Subject to any disclaimer, the term of this patent is extended or adjusted under 35 U.S.C. 154(b) by 380 days.

(21) Appl. No.: 17/612,973

(22) PCT Filed: May 29, 2020

(86) PCT No.: PCT/US2020/035113
§ 371 (c)(1),
(2) Date: Nov. 19, 2021

(87) PCT Pub. No.: WO2020/243425
PCT Pub. Date: Dec. 3, 2020

(65) Prior Publication Data
US 2022/0215539 A1   Jul. 7, 2022

Related U.S. Application Data

(60) Provisional application No. 62/893,043, filed on Aug. 28, 2019, provisional application No. 62/855,755, filed on May 31, 2019.

(51) Int. Cl.
G06T 7/00     (2017.01)
A61B 90/00    (2016.01)
(Continued)

(52) U.S. Cl.
CPC ............ *G06T 7/0012* (2013.01); *A61B 90/37* (2016.02); *G06T 7/11* (2017.01); *G06V 10/16* (2022.01);
(Continued)

(58) Field of Classification Search
CPC ................. G06T 7/0012; G06T 7/11; G06T 2207/10064; G06T 2207/10132;
(Continued)

(56) References Cited

U.S. PATENT DOCUMENTS

2002/0140709 A1   10/2002   Sauer et al.
2006/0267977 A1*  11/2006   Barfuss .................... G06T 7/33
                                                     345/419

(Continued)

FOREIGN PATENT DOCUMENTS

CN    1864633 A     11/2006
CN    102781336 A   11/2012
(Continued)

OTHER PUBLICATIONS

International Search Report and Written Opinion for Application No. PCT/US2020/035113, mailed Sep. 18, 2020, 11 pages.

(Continued)

*Primary Examiner* — Khai M Nguyen

(57) ABSTRACT

A composite medical imaging system may direct a display device to display an image captured by an imaging device and showing a view of a surgical area and display an augmentation region within the image and that shows supplemental content. The view of the surgical area shows surface anatomy located at the surgical area and an object located at the surgical area. The augmentation region creates an occlusion over at least a portion of the view of the surgical area. The system may detect an overlap in the image between at least a portion of the object and at least a portion (Continued)

of the augmentation region. In response to the detection of the overlap, the system may adjust the image to decrease an extent of the occlusion within the overlap by the augmentation region.

20 Claims, 11 Drawing Sheets

(51) Int. Cl.
  *G06T 7/11* (2017.01)
  *G06V 10/10* (2022.01)
  *G06V 10/25* (2022.01)
  *G06V 10/26* (2022.01)

(52) U.S. Cl.
  CPC .............. *G06V 10/25* (2022.01); *G06V 10/26* (2022.01); *A61B 2090/376* (2016.02); *G06T 2207/10064* (2013.01); *G06T 2207/10132* (2013.01)

(58) Field of Classification Search
  CPC .. A61B 90/37; A61B 2090/376; G06V 10/25; G06V 10/16; G06V 10/26
  See application file for complete search history.

(56) References Cited

U.S. PATENT DOCUMENTS

| | | | |
|---|---|---|---|
| 2008/0030578 | A1 | 2/2008 | Razzaque et al. |
| 2013/0322717 | A1 | 12/2013 | Bar-Shalev |
| 2014/0303491 | A1* | 10/2014 | Shekhar ................. G06T 7/337 600/424 |
| 2017/0007350 | A1* | 1/2017 | Popovic ................. A61B 34/10 |
| 2019/0060001 | A1* | 2/2019 | Kohli ..................... A61B 34/20 |

FOREIGN PATENT DOCUMENTS

| | | |
|---|---|---|
| CN | 102999938 A | 3/2013 |
| CN | 103371870 A | 10/2013 |
| CN | 105979900 A | 9/2016 |
| CN | 108882854 A | 11/2018 |
| WO | WO-2007047782 A2 | 4/2007 |
| WO | WO-2019006028 A1 | 1/2019 |

OTHER PUBLICATIONS

International Search Report and Written Opinion for Application No. PCT/US2020/035125, mailed Sep. 22, 2020, 11 pages.
Vertut, J, and Coiffet, P., "Robot Technology: Teleoperation and Robotics Evolution and Development," English translation, Prentice-Hall, Inc., Inglewood Cliffs, NJ, USA 1986, vol. 3A, 332 pages.
Office Action for Chinese Application No. CN202080052031.5, mailed Jul. 29, 2023, 28 pages.
International Preliminary Report on Patentability for Application No. PCT/US2020/035113 mailed on Dec. 9, 2021, 9 pages.
International Preliminary Report on Patentability for Application No. PCT/US2020/035125 mailed on Dec. 9, 2021, 9 pages.
Lerotic M., et al., "pq-space Based Non-Photorealistic Rendering for Augmented Reality," Medical Image Computing and Computer-Assisted Intervention, 2007, vol. 10 (Pt 2), pp. 102-109.
Office Action for Chinese Application No. CN202080052031.5, mailed Jul. 5, 2024, 36 pages.
Bichlmeier C., "Immersive, Interactive and Contextual In-situ Visualization for Medical Applications," Computer Science, Engineering, Medicine, 2010, pp. 1-189, Retrieved from the Internet: [URL: https://mediatum.ub.tum.de/doc/977862/977862.pdf].

* cited by examiner

Fig. 4A
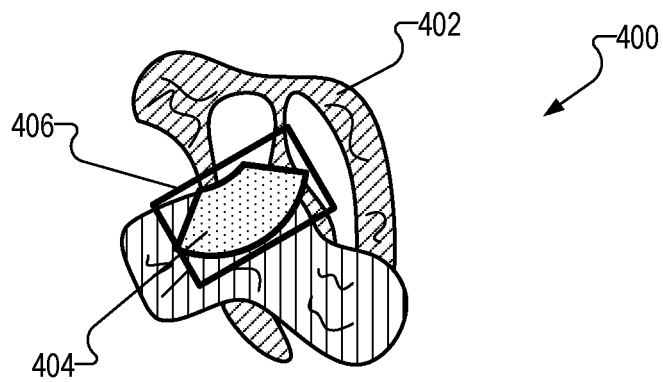
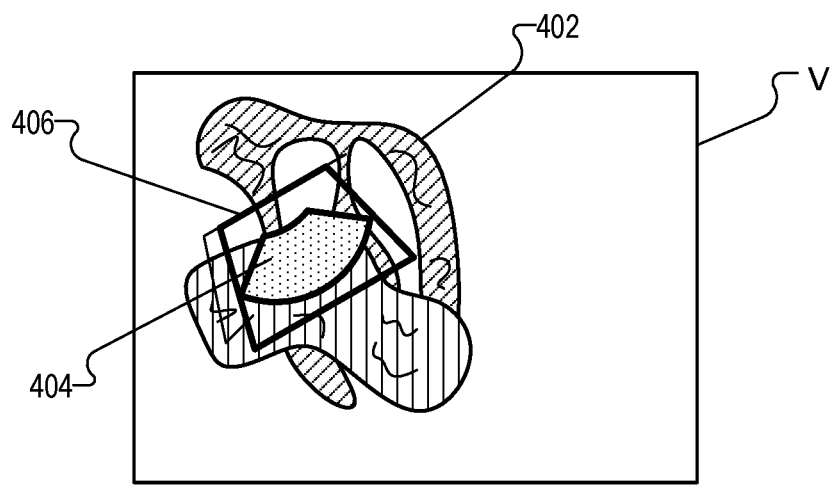
Fig. 4B
Fig. 4C

COMPOSITE MEDICAL IMAGING SYSTEMS AND METHODS

RELATED APPLICATIONS

The present application is a U.S. National Stage Application under 35 U.S.C. § 371 of International Application No. PCT/US2020/035113, filed on May 29, 2020, which claims priority to U.S. Provisional Patent Application No. 62/893,043, filed on Aug. 28, 2019, and to U.S. Provisional Patent Application No. 62/855,755, filed on May 31, 2019, the contents of which are hereby incorporated by reference in their entirety.

BACKGROUND INFORMATION

An imaging device (e.g., an endoscope) may be used during a surgical procedure to capture images of a surgical area associated with a patient. The images may be presented (e.g., in the form of a video stream) to a surgeon during the surgical procedure to assist the surgeon in performing the surgical procedure. In some examples, supplemental content such as ultrasound images may also be presented during the surgical procedure. However, there remains room to improve the presentation of the supplemental content so as to not interfere with the surgical procedure.

SUMMARY

The following description presents a simplified summary of one or more aspects of the methods and systems described herein in order to provide a basic understanding of such aspects. This summary is not an extensive overview of all contemplated aspects, and is intended to neither identify key or critical elements of all aspects nor delineate the scope of any or all aspects. Its sole purpose is to present some concepts of one or more aspects of the methods and systems described herein in a simplified form as a prelude to the more detailed description that is presented below.

An exemplary system may comprise a memory storing instructions and a processor communicatively coupled to the memory and configured to execute the instructions to direct a display device to display an image showing a view of a surgical area associated with a patient as captured by an imaging device, the view of the surgical area showing surface anatomy located at the surgical area and an object located at the surgical area, and an augmentation region that shows supplemental content, the augmentation region creating an occlusion over at least a portion of the view of the surgical area; detect an overlap in the image between at least a portion of the object and at least a portion of the augmentation region; and adjust, in response to the detection of the overlap, the image to decrease an extent of the occlusion within the overlap by the augmentation region.

An exemplary method may comprise directing, by a composite medical imaging system, a display device to display an image showing a view of a surgical area associated with a patient as captured by an imaging device, the view of the surgical area showing surface anatomy located at the surgical area and an object located at the surgical area, and an augmentation region that shows supplemental content, the augmentation region creating an occlusion over at least a portion of the view of the surgical area; detecting, by the composite medical imaging system, an overlap in the image between at least a portion of the object and at least a portion of the augmentation region; and adjusting, by the composite medical imaging system and in response to the detection of the overlap, the image to decrease an extent of the occlusion within the overlap by the augmentation region.

An exemplary non-transitory computer-readable medium may store instructions that, when executed, direct at least one processor of a computing device to direct a display device to display an image showing a view of a surgical area associated with a patient as captured by an imaging device, the view of the surgical area showing surface anatomy located at the surgical area and an object located at the surgical area, and an augmentation region that shows supplemental content, the augmentation region creating an occlusion over at least a portion of the view of the surgical area; detect an overlap in the image between at least a portion of the object and at least a portion of the augmentation region; and adjust, in response to the detection of the overlap, the image to decrease an extent of the occlusion within the overlap by the augmentation region.

BRIEF DESCRIPTION OF THE DRAWINGS

The accompanying drawings illustrate various embodiments and are a part of the specification. The illustrated embodiments are merely examples and do not limit the scope of the disclosure. Throughout the drawings, identical or similar reference numbers designate identical or similar elements.

FIG. 30 illustrates an exemplary slope image generated based on the endoscopic image of FIG. 3B according to principles described herein.

FIG. 4A illustrates an exemplary virtual surgical area according to principles described herein.

FIG. 4B illustrates an exemplary virtual image of the virtual surgical area of FIG. 4A as captured by a virtual imaging device according to principles described herein, FIG. 4C illustrates an exemplary mask image generated based on the virtual image of FIG. 4B according to principles described herein.

DETAILED DESCRIPTION

Figure 1:
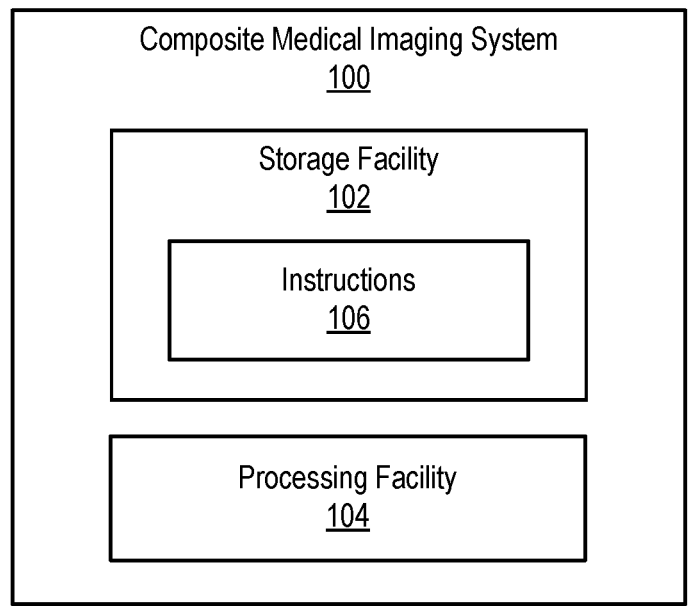
FIG. 1 illustrates an exemplary composite medical imaging system according to principles described herein.

Composite medical imaging systems and methods are described herein. As will be explained in more detail below, an exemplary composite medical imaging system may direct a display device to display an image that shows a view of a surgical area associated with a patient, as captured by an imaging device included in a computer-assisted surgical system, and an augmentation region. The view of the surgical area shows surface anatomy located at the surgical area and an object located at the surgical area (e.g., a surgical instrument or a pool of blood), and the augmentation region shows supplemental content. The augmentation region creates an occlusion over at least a portion of the view of the surgical area. The system may also detect an overlap in the image between at least a portion of the object and at least a portion of the augmentation region. In response to the detection of the overlap, the system may adjust the image to decrease an extent of the occlusion within the overlap by the augmentation region.

To illustrate, during a minimally-invasive surgical procedure performed with a computer-assisted surgical system, a surgeon positioned at a user control system may teleoperate an ultrasound probe and a cautery instrument to perform a surgical procedure on a patient. An endoscope may capture an image of a surgical area associated with the patient, and a display device of the user control system may present the captured image to the surgeon to provide a visualization of the surgical area. When the ultrasound probe contacts surface anatomy at the surgical area, an ultrasound image may be generated that represents subsurface anatomy located beneath the surface anatomy contacted by the ultrasound probe. The ultrasound image is then displayed in an augmentation region of the image presented by the display device. The augmentation region creates an occlusion over the captured endoscopic image. In this example, the augmentation region is a region of the displayed image that appears to "cut" into or "open" the surface anatomy to show a representation (e.g., the ultrasound image) of subsurface anatomy located beneath the portion of the surface anatomy that is within the occlusion created by the augmentation region. The augmentation region may project from and be movable with the ultrasound probe, thus allowing the surgeon to see subsurface anatomy beneath the surface anatomy at any desired location in the surgical area by controlling the location of the ultrasound probe.

While the ultrasound image is displayed in the augmentation region, the surgeon may move the cautery instrument such that a view of the cautery instrument overlaps with the augmentation region in the image displayed by the display device. When the view of the cautery instrument overlaps with the augmentation region in the displayed image, the augmentation region (or a portion of the augmentation region within the overlap) and the corresponding ultrasound image may be removed from the displayed image and only the image captured by the endoscope is presented. Thus, the surgeon may easily see the surface anatomy at the location near the cautery instrument.

The systems and methods described herein may provide various benefits. For example, the systems and methods described herein may intelligently present, in a viewable image presented to a user (e.g., a surgeon) during a surgical procedure, an augmentation region that shows supplemental content (e.g., a representation of subsurface anatomy, such as an image of a three-dimensional model of anatomy or an ultrasound image). In this way the systems and methods present useful information (e.g., information about the patient's subsurface anatomy) and provide an improved visual experience for the user during the surgical procedure. Additionally, the systems and methods described herein may intelligently prevent the augmentation region and the supplemental content from being included in the viewable image when an object in the image (e.g., a surgical instrument, a pool of blood, etc.) overlaps with the augmentation region. In this way the systems and methods provide a view of the surface anatomy to facilitate performance of the surgical procedure. These and other benefits of the systems and methods described herein will be made apparent in the description that follows.

FIG. 1 illustrates an exemplary composite medical imaging system 100 ("system 100") that may be configured to present a composite medical image. System 100 may be included in, implemented by, or connected to any surgical systems or other computing systems described herein. For example, system 100 may be implemented by a computer-assisted surgical system. As another example, system 100 may be implemented by a stand-alone computing system communicatively coupled to a computer-assisted surgical system.

As shown, system 100 may include, without limitation, a storage facility 102 and a processing facility 104 selectively and communicatively coupled to one another. Facilities 102 and 104 may each include or be implemented by hardware and/or software components (e.g., processors, memories, communication interfaces, instructions stored in memory for execution by the processors, etc.). For example, facilities 102 and 104 may be implemented by any component in a computer-assisted surgical system. In some examples, facilities 102 and 104 may be distributed between multiple devices and/or multiple locations as may serve a particular implementation.

Storage facility 102 may maintain (e.g., store) executable data used by processing facility 104 to perform any of the operations described herein. For example, storage facility 102 may store instructions 106 that may be executed by processing facility 104 to perform any of the operations described herein. Instructions 106 may be implemented by any suitable application, software, code, and/or other executable data instance. Storage facility 102 may also maintain any data received, generated, managed, used, and/or transmitted by processing facility 104.

Processing facility 104 may be configured to perform (e.g., execute instructions 106 stored in storage facility 102 to perform) various operations associated with presenting a composite medical image. For example, processing facility 104 may be configured to direct a display device to display an image showing a view of a surgical area associated with a patient as captured by an imaging device included in a computer-assisted surgical system, the view of the surgical area showing surface anatomy located at the surgical area and an object located at the surgical area The image also shows an augmentation region that shows supplemental content, the augmentation region creating an occlusion over at least a portion of the view of the surgical area. Processing facility 104 may further be configured to detect an overlap in the image between at least a portion of the object and at least a portion of the augmentation region. Processing facility 104 may also be configured to adjust, in response to the detection of the overlap, the image to decrease an extent of the occlusion within the overlap by the augmentation region. These and other operations that may be performed by processing facility 104 are described herein. In the description that follows, any references to operations performed by system 100 may be understood to be performed by processing facility 104 of system 100.

Figure 2:
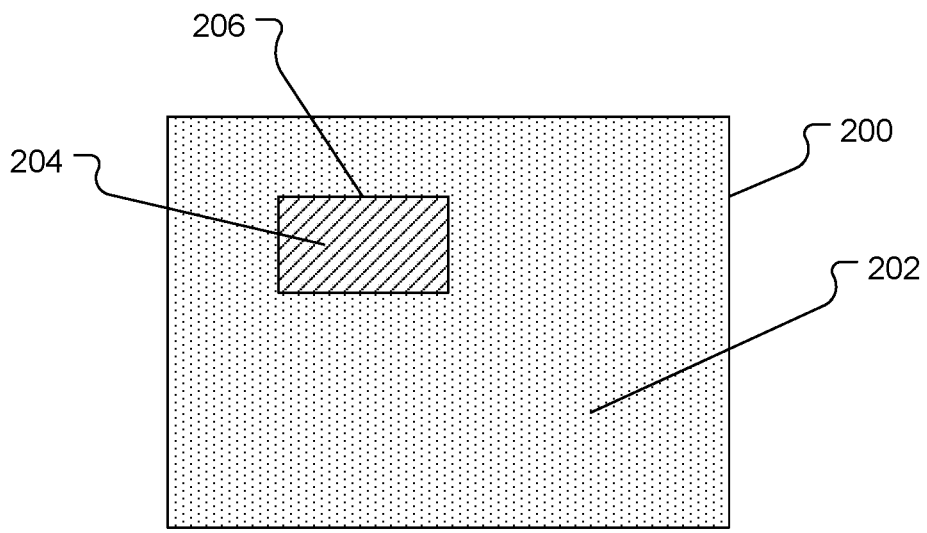
FIG. 2 illustrates an exemplary composite medical image according to principles described herein.

System 100 is configured to direct a display device to display a composite medical image. As used herein, a composite medical image includes a surgical area image and an augmentation region. The augmentation region creates an occlusion over at least a portion of the surgical area image (e.g., is opaque or at least partially transparent), and may show (e.g., include or be populated with) any supplemental content as may suit a particular implementation. FIG. 2 illustrates an exemplary composite medical image 200 ("image 200"). As shown, composite medical image 200 shows a surgical area image 202 and supplemental content 204 presented in augmentation region 206 of surgical area image 202.

Surgical area image 202 shows a view of a surgical area associated with a patient, as captured by an imaging device (e.g., an endoscope). A "surgical area" may, in certain examples, be entirely disposed within a patient and may include an area within the patient at or near where a surgical procedure is planned to be performed, is being performed, or has been performed. For example, for a minimally invasive surgical procedure being performed on tissue internal to a patient, the surgical area may include the surface anatomy (e.g., surface tissue), subsurface anatomy underlying the surface anatomy (e.g., organs and vasculature underneath or behind the surface tissue), as well as space around the tissue where, for example, surgical instruments being used to perform the surgical procedure are located. In other examples, a surgical area may be at least partially disposed external to the patient at or near where a surgical procedure is planned to be performed, is being performed, or has been performed on the patient. For example, for an open surgical procedure, part of the surgical area (e.g., tissue being operated on) may be internal to the patient while another part of the surgical area (e.g., a space around the tissue where one or more surgical instruments may be disposed) may be external to the patient.

As used herein, "surface anatomy" (sometimes referred to herein as "surface tissue") may be disposed internally to the patient (e.g., organs, tissue, vasculature, etc.) or may be disposed externally to the patient (e.g., skin, etc.). In some examples the view of the surgical area shows surface anatomy located at the surgical area by capturing light reflected from the surface anatomy. In these examples surface anatomy refers to anatomy configured to reflect light to the imaging device. Additionally, as used herein, "subsurface anatomy" is disposed internally to the patient and is located beneath or behind surface anatomy, with respect to the view of the surface anatomy captured by the imaging device, and thus is not configured to reflect light to the imaging device.

Supplemental content 204 may include any suitable content configured to augment surgical area image 202, such as but not limited to other medical images (e.g., images generated by fluorescence imaging, ultrasound imaging, computed tomography (CT), optical coherence tomography (OCT), magnetic resonance imaging (MRI), x-ray imaging, and the like), textual content (e.g., labels, surgical procedure information, surgical system information, patient information, messages, etc.), non-medical images (e.g., instructional images or videos, etc.), and the like. In some examples supplemental content 204 is a representation of subsurface anatomy of the patient, such as an ultrasound image, an x-ray image, a fluorescence image, an image of a three-dimensional model generated from a CT scan or MRI scan of the patient, and the like. In other aspects supplemental content 204 may include a combination (e.g., a blending) of multiple different types of supplemental content.

While FIG. 2 shows only one instance of supplemental content 204 and one augmentation region 206, image 200 may include any number of distinct instances of supplemental content and/or augmentation regions as may suit a particular implementation. Additionally, while FIG. 2 shows that augmentation region 206 is rectangular, augmentation region 206 may be any shape or size as may suit a particular implementation, Additionally, while FIG. 2 shows that augmentation region 206 is opaque, augmentation region 206 may be semi-transparent and thus show a blending of supplemental content 204 and the portion of surgical area image 202 occluded by augmentation region 206.

In some examples augmentation region 206 may be movable within image 200 based on user input. For instance, a user (e.g., a surgeon) may manipulate a user input device to change a position of augmentation region 206 within image 200, In this way the user may view supplemental content 204 at any desired location within image 200.

In some examples system 100 may be configured generate composite medical image 200. Alternatively, composite medical image 200 may be generated by a computing system communicatively coupled to system 100 (e.g., a computing system included in a computer-assisted surgical system). Composite medical image 200 may be generated in any suitable way.

FIG. 3A-FIG. 5 illustrate an exemplary manner of generating a composite medical image during a minimally-invasive surgical procedure performed on a patient. However, it will be recognized that the principles that follow may be applied to any other type of surgical procedure, such as an open surgical procedure, a training procedure, a testing procedure, and the like. Additionally, it will be understood that a composite medical image may be generated by any other suitable method as may suit a particular implementation.

Figure 3A:
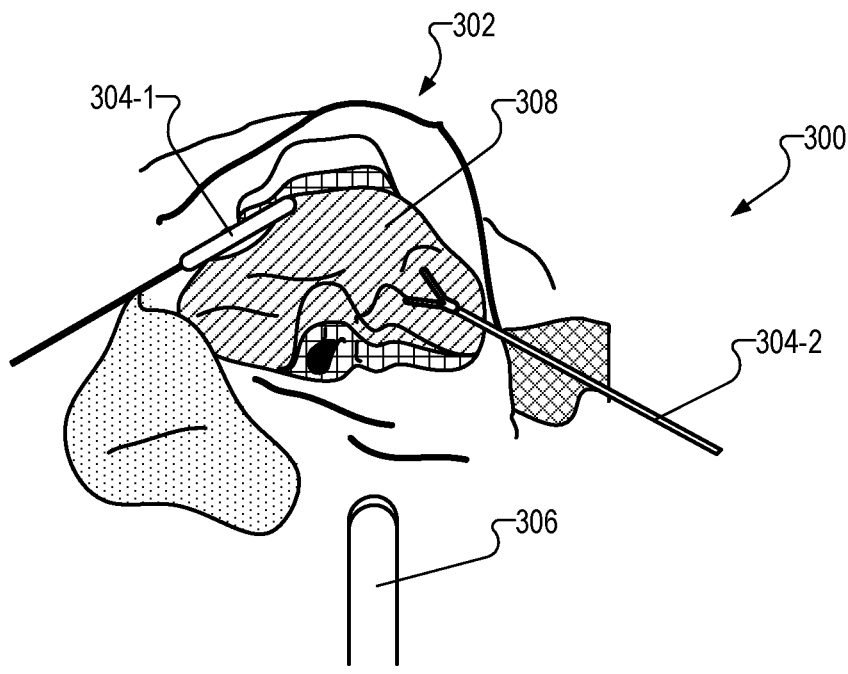
FIG. 3A illustrates an exemplary surgical area associated with a patient according to principles described herein.

FIG. 3A illustrates an exemplary surgical area 300 associated with a patient. As shown, surgical area 300 includes patient anatomy 302, surgical instruments 304 (e.g., ultrasound probe 304-1 and scissors 304-2), and an imaging device 306 (e.g., an endoscope). Patient anatomy 302 may represent any organ or anatomical feature of the patient, and may include surface anatomy 308 (e.g., surface tissue) and subsurface anatomy (e.g., subsurface tissue, organs, vasculature, etc.) (not shown in FIG. 3A).

Ultrasound probe 304-1 is configured to capture an ultrasound image by emitting sound waves and detecting the sound waves reflected from subsurface anatomy beneath surface anatomy 308. Scissors 304-2 are configured to cut patient tissue. Surgical instruments 304 may have any suitable shape and/or size as may serve a particular implementation In some examples, surgical instruments 304 may have a shape and size that allow surgical instruments 304 to be inserted into the patient by way of a port in a body wall of the patient. In these examples, a movement and operation of surgical instruments 304 within the patient may be controlled manually (e.g., by manually manipulating a shaft to which ultrasound probe 304-1 or scissors 304-2 are connected). Additionally or alternatively, surgical instruments 304 may be controlled in a computer-assisted manner (e.g., by a computer-assisted surgical system that utilizes robotic and/or teleoperation technology).

In some examples, the poses (e.g., the positions and/or orientations) of surgical instruments 304 in surgical area 300 may be tracked by a computer-assisted surgical system. For instance, surgical instruments 304 may include one or more sensors (e.g., displacement transducers, orientational sensors, positional sensors, etc.) used to generate kinematics information. Kinematics information may include information such as pose (e.g., position and/or orientation), movement (e.g., velocity, direction, acceleration, etc.), state (e.g., open, closed, stowed, etc.), and/or other attributes of surgical instruments 304, all of which may be tracked by a computer-assisted surgical system.

Imaging device 306 is implemented by a stereoscopic endoscope configured to capture stereoscopic images of surgical area 300. However, it will be understood that imaging device 306 may be implemented by any other suitable imaging device. In some examples imaging device 306 may be coupled to a computer-assisted surgical system and controlled in a computer-assisted manner. Image data representative of one or more images captured by imaging device 306 may constitute one or more still images and/or video captured by imaging device 306.

Figure 3B:
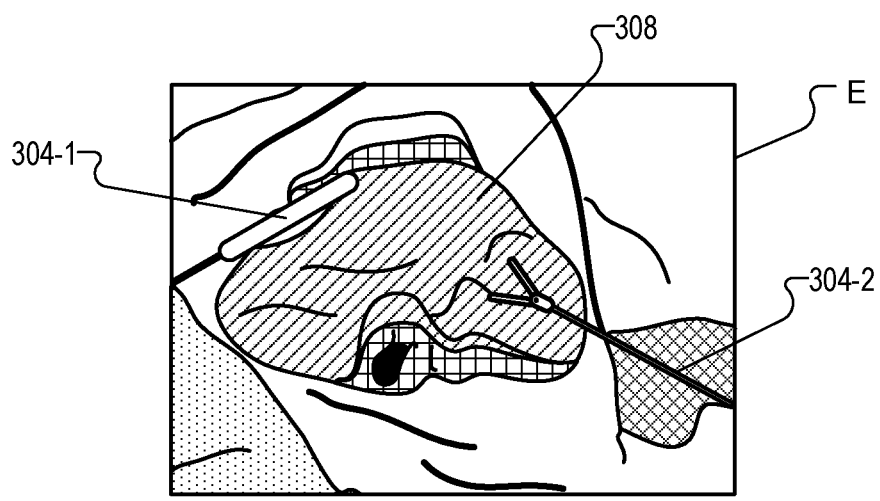
FIG. 3B illustrates an exemplary endoscopic image of the surgical area of FIG. 3A as captured by an imaging device located at the surgical area according to principles described herein.

FIG. 3B illustrates an exemplary endoscopic image E as captured by imaging device 306. Endoscopic image E has I×J pixels and represents only one of a pair of stereoscopic images (e.g., a left eye image or a right eye image). It will be understood that the description that follows applies equally to the other of the pair of stereoscopic images captured by imaging device 306, Similarly, the description that follows may also apply to monoscopic images captured by imaging device 306, As shown in FIG. 3B, endoscopic image E shows a view of surgical area 300 as captured by imaging device 306. Endoscopic image E may be generated by illuminating surgical area 300 and capturing light reflected by surface anatomy 308 and surgical instruments 304 to imaging device 306, Thus, the view of surgical area 300 shows a view of surgical instruments 304 and surface anatomy 308 located at surgical area 300.

Figure 3C:

In some examples a slope image may be generated from endoscopic image E, As will be explained below in more detail, a slope image may be used in the generation of a composite medical image to enhance depth perception by a user. However, a slope image may be omitted from the composite medical image in other examples. FIG. 3C illustrates an exemplary slope image S generated from endoscopic image E. Slope image S is illustrated in black and white in FIG. 30. However, slope image S may include black, white, and/or gray in various shades that represent degrees of slope. Slope image S is generated based on a gradient of endoscopic image E, and thus will have the same size (I×J pixels) as endoscopic image E. Slope image S may be generated in any suitable way using any suitable algorithm. In some examples slope image S is generated from the horizontal and/or vertical components of the gradient of endoscopic image E. For instance, a pixel value $S_{(i,j)}$ in slope image S may be set as the value of the next horizontally adjacent pixel $E_{(i+1,j)}$ in endoscopic image E less the value of the pixel $E_{(i,j)}$ in endoscopic image E. If $S_{(i,j)}$ is less than zero then $S_{(i,j)}$ is set to zero. For pixels at the far right edge where there is no horizontally adjacent pixel, the value of the next horizontally adjacent pixel $E_{(i+1,j)}$ may be set to a predetermined value (e.g., black, an average value of pixels in a surrounding region, etc.). This process may be performed for each pixel until slope image S is completed.

Referring now to FIG. 4A, a three-dimensional ("3D") virtual surgical area 400 is generated. Virtual surgical area 400 includes one or more representations of subsurface anatomy located beneath surface anatomy 308 at surgical area 300. For example, as shown in FIG. 4A, virtual surgical area 400 includes a 3D model 402 of subsurface anatomy (e.g., a 3D model of subsurface anatomy generated based on pre-operative MRI and/or CT scan imaging) and an ultrasound image 404 generated by ultrasound probe 304-1. Ultrasound image 404 represents subsurface anatomy located beneath surface anatomy 308. As shown in FIG. 4A, virtual surgical area 400 also includes a frame 406 onto which ultrasound image 404 is projected, such as by texture mapping. Frame 406 will be described below in more detail. It will be recognized that any one or more of 3D model 402, ultrasound image 404, and frame 406 may be omitted from virtual surgical area 400 without departing from the scope of this disclosure.

Virtual surgical area 400 also includes a virtual imaging device 408 configured to "capture" an image of virtual surgical area 400. FIG. 4B illustrates an exemplary virtual image V ("virtual image V") as captured by virtual imaging device 408. As shown in FIG. 4A, a pose (e.g., position and orientation) of virtual imaging device 408 within virtual surgical area 400 determines the view of virtual surgical area 400, including the view of 3D model 402, ultrasound image 404, and frame 406, as depicted in virtual image V.

In some examples the view of virtual surgical area 400 as captured by virtual imaging device 408 may be registered with the view of surgical area 300 as captured by imaging device 306. In other words, 3D model 402 and ultrasound image 404 may be positioned and oriented within virtual surgical area 400 such that; in composite medical image C ("composite image C") that combines endoscopic image E and virtual image V (see FIG. 5), 3D model 402 and/or ultrasound image 404 appear to be located at their actual, physical location in the patient's body relative to surface anatomy 308. Any suitable registration technique may be used to register the view of virtual surgical area 400 as captured by virtual imaging device 408 with the view of surgical area 300 as captured by imaging device 306. In some examples registration may be based on a depth map of surgical area as generated based on images captured by imaging device 306. A pose of virtual imaging device 408 in virtual surgical area 400 may be configured to change in accordance with a change in pose of imaging device 306 in surgical area 300 to thereby maintain the registration of virtual image V with endoscopic image E. In some examples virtual imaging device 302 is also configured with the same camera properties (e.g., resolution, zoom level, focus, etc.) as imaging device 306.

As shown in FIG. 4A, frame 406 is a frame that is positioned and oriented within virtual surgical area 400. As will be described below in more detail, frame 406 may be used to define an augmentation region in composite image C that provides a view of the representations of subsurface anatomy (e.g., 3D model 402 and/or ultrasound image 404).

Frame 406 may be selectively movable within virtual surgical area 400 based on user input In some examples a pose of frame 406 within virtual surgical area 400 may be based on a pose of a surgical instrument 304 located at surgical area 300. As an example, a position of frame 406 in virtual surgical area 400 may be based on a position of ultrasound probe 304-1 in surgical area 300, and the orientation of frame 406 (e.g., the direction of the plane of frame 406) within virtual surgical area 400 is based on the orientation (e.g. rotation) of ultrasound probe 304-1 in surgical area 300. For instance, frame 406 may be oriented in the direction in which ultrasound probe 304-1 emits and receives ultrasound signals, thereby ensuring that ultrasound image 404 generated by ultrasound probe 304-1 accurately represents subsurface anatomy located beneath surface anatomy 308 when projected onto frame 406.

As shown in FIG. 4B, virtual image V shows a view of virtual surgical area 400, including 3D model 402, ultrasound image 404, and frame 406, as captured by virtual imaging device 408. Thus, the view of virtual surgical area 400 in virtual image V shows a view of representations of subsurface anatomy located at surgical area 300. In some examples virtual image V is the same size (I×J pixels) as endoscopic image E.

A mask image M is then generated from virtual image V. FIG. 4C illustrates an exemplary mask image M. Mask image M is set to be the same size (I×J pixels) as virtual image V and includes a mask region 410 and a window region 412. The size, shape, and position of window region 412 determines the size, shape, and position of the augmentation region included in composite image C. As shown in FIGS. 4B and 4C, the view of ultrasound image 404 projected onto frame 406 in virtual image V sets the size, shape, and position of window region 412 in mask image M. In alternative embodiments, the view of frame 406 in virtual image V may set the size, shape, and position of window region 412 in mask image M.

In some embodiments all pixels in mask region 410 are set to display black while all pixels in window region 412 are set to display white. For example, where a pixel value ranges from 0 (black) to 1 (white), a value of a pixel $M_{(i,j)}$ is set to 0 if the corresponding pixel $V_{(i,j)}$ in virtual image V is not included in the view of ultrasound image 404, and the value of pixel $M_{(i,j)}$ is set to 1 (white) if the corresponding pixel $V_{(i,j)}$ in virtual image V is included in the view of ultrasound image 404. With this arrangement, mask image M is configured to mask all pixels in virtual image V that do not overlap with a view of ultrasound image 404 in virtual image V.

Figure 5:
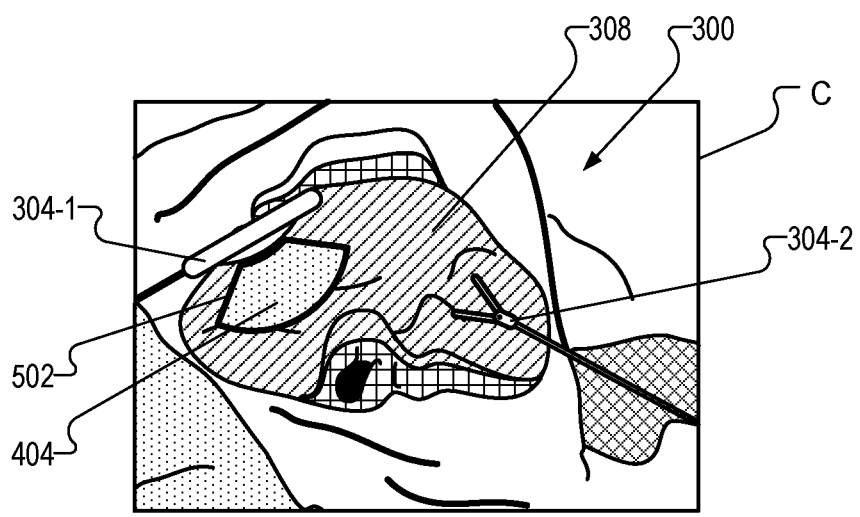
FIG. 5 illustrates an exemplary composite medical image displayed by a display device according to principles described herein.

Composite image C is generated by combining images E, S, V, and M. FIG. 5 illustrates an exemplary composite image C having the same size (I×J pixels) as endoscopic image E captured by imaging device 306. Composite image C may be generated in any suitable way. In some examples, composite image C is generated by blending images E, S, V, and M by setting the value of each pixel $C_{(i,j)}$ according to the following equation [1];

$$C_{(i,j)}=M_{(i,j)}*(S_{(i,j)}+V_{(i,j)})+(1-M_{(i,j)})*E_{(i,j)} \quad [1]$$

Thus, where $M_{(i,j)}=0$ (i.e., the pixel $M_{(i,j)}$ in mask image M is 0, i.e. black), the value of pixel $C_{(i,j)}$ in composite image C is the value of pixel $E_{(i,j)}$. That is, mask region 410 of mask image M masks slope image S and virtual image V so that only the endoscopic image E captured by imaging device 306 is displayed. However, where $M_{(i,j)}=1$ (i.e., the pixel $M_{(i,j)}$ in mask image M is 1, i.e., white), the value of pixel $C_{(i,j)}$ in composite image C is the value of $S_{(i,j)}+V_{(i,j)}$. That is, window region 412 of mask image M provides an opaque augmentation region in endoscopic image E where only a combination of slope image S and virtual image V are displayed, such that the augmentation region creates an occlusion of a corresponding region of endoscopic image E.

In alternative embodiments, the augmentation region may be transparent. The augmentation region may be made transparent by any suitable method. For example, the value of pixel $M_{(i,j)}$ may be set to be less than 1 (e.g., 0.85) if the corresponding pixel $V_{(i,j)}$ in virtual image V is included in the view of ultrasound image 404. According to equation [1], when $M_{(i,j)}<1$ the value of pixel $C_{(i,j)}$ in composite image C is a blended combination of $S_{(i,j)}$, $V_{(i,j)}$ and $E_{(i,j)}$. That is, window region 412 of mask image M provides a transparent augmentation region that creates only a partial occlusion of the corresponding region of endoscopic image E. In some examples, the transparency of the augmentation region may be automatically or manually adjusted (e.g., increased or decreased) to adjust the extent of occlusion of the corresponding region of endoscopic image E.

As shown in FIG. 5, composite image C shows a view of surgical area 300 associated with a patient and an augmentation region 502. The view of surgical area 300 shows surgical instruments 304 (e.g., ultrasound probe 304-1 and scissors 304-2) and surface anatomy 308 located at surgical area 300, while augmentation region 502 shows a representation of subsurface anatomy (e.g., ultrasound image 404). In embodiments where augmentation region 502 is created based on frame 406, augmentation region 502 additionally or alternatively shows a view of 3D model 402. Furthermore, because the view of 3D model 402 and ultrasound image 404 is registered with the view of surgical area 300, as explained above, 3D model 402 and ultrasound image 404 provide an accurate representation of subsurface anatomy at the in-vivo location of the subsurface anatomy represented by 3D model 402 and ultrasound image 404.

As mentioned, slope image S is generated based on the gradient of endoscopic image E. As a result, combining slope image S with virtual image V in augmentation region 502 enhances the perception by a viewer of composite image C that 3D model 402 and/or ultrasound image 404 are located beneath surface anatomy 308. However, slope image S may be omitted from composite image C such that augmentation region 502 shows only virtual image V in other examples.

In composite image C, augmentation region 502 is depicted as projecting from ultrasound probe 304-1, similar in appearance to a flag projecting from a flagpole. In alternative embodiments, augmentation region 502 projects from a different type of surgical instrument located in surgical area 300 or from a virtual surgical instrument rather than a real surgical instrument located in surgical area 300. For instance, virtual surgical area 400 may include a virtual surgical instrument (not shown in FIGS. 4A-4C) that may be controlled based on user input. Ultrasound image 404 and/or frame 406 are positioned in virtual surgical area 400 based on the pose of the virtual surgical instrument in virtual surgical area 400.

In further embodiments augmentation region 502 does not project from any surgical instrument, real or virtual, but is movable based on user input. For instance, a user may selectively operate a controller (e.g., a joystick, a master control, etc.) to move the position of frame 306 in virtual surgical area 400, thereby also moving augmentation region 502 in composite image C. In this way the user may move augmentation region 502 to view subsurface anatomy without having to move a surgical instrument located in surgical area 300.

As mentioned, FIGS. 4C and 5 show that mask image M sets a shape of augmentation region 502 to be the same shape as the view of ultrasound image 404 in virtual image V. In alternative embodiments, mask image M sets a shape of augmentation region 502 to be the same shape as the view of frame 306 in virtual image V. This configuration may be used when ultrasound image 404 is not projected onto frame 306, thereby showing 3D model 402 through augmentation region 502 in composite image C. Alternatively, when ultrasound image 404 is projected onto frame 306, 3D model 402 may be displayed in the regions of frame 406 that are not covered by ultrasound image 404.

As mentioned, system 100 may direct a display device to display composite image C. For instance, system 100 may direct a display device associated with a computer-assisted surgical system to display composite image C upon user activation of a composite image mode. The display device may be any suitable display device, such as a display device of a user control system used by a surgeon during a computer-assisted surgical procedure.

While composite image C is displayed, system 100 may detect an overlap in composite image C between at least a portion of an object located at surgical area 300 and at least a portion of augmentation region 502. The object located at the surgical area may include any foreign object introduced to surgical area 300 (e.g., a surgical instrument, a surgical mesh, a hand or finger of a surgeon, etc.) and/or any object naturally present at the surgical area (e.g., blood, tissue, an organ, etc.). For instance, system 100 may detect that a surgical instrument has moved such that a view of the surgical instrument overlaps with a portion of augmentation region 502 in composite image C. As another example, system 100 may detect that a view of a pool of blood overlaps with a portion of augmentation region 502 in composite image C.

In response to detecting the overlap between the portion of the object and the portion of augmentation region 502, system 100 may adjust the displayed image to decrease an extent of the occlusion within the overlap by augmentation region 502. In some examples system 100 may adjust the displayed image by removing the augmentation region from the image. For instance, system 100 may switch from displaying composite image C to displaying another image (e.g., endoscopic image E', see FIG. 6C) that does not show augmentation region 502. Thus, augmentation region 502 does not occlude the view of surgical area 300 as captured by the imaging device. As another example, system 100 may decrease the size and/or shape of augmentation region 502, such as by removing a portion of augmentation region 502 within a predefined vicinity of the object (e.g., within the region of the overlap).

As another example of adjusting the displayed image to decrease the extent of the occlusion, system 100 may decrease the opacity of augmentation region 502 in composite image C. For example, system 100 may adjust the blending of images E, S, V, and M so that augmentation region 502 is more transparent. In some examples the degree of transparency may be modulated, such as based on a distance of the object to the surface anatomy and/or based on a type of object that overlaps with augmentation region 502. Additionally or alternatively, system 100 may adjust the blending of images E, S, V, and M only within an area located within a predefined vicinity of the object (e.g., within the region of the overlap).

As a further example of decreasing the opacity of augmentation region 502, system 100 may adjust slope image S to be more visible in augmentation region 502. For instance, system 100 may adjust one or more parameters of an image filter for slope image S. Because slope image S is derived from endoscopic image E, increasing the visibility of slope image S will increase the visibility of the view of surgical area 300 as captured by the imaging device. In this way system 100 may adjust composite image C to decrease an extent of the occlusion of the view of surgical area 300 by augmentation region 502.

Figure 6A:
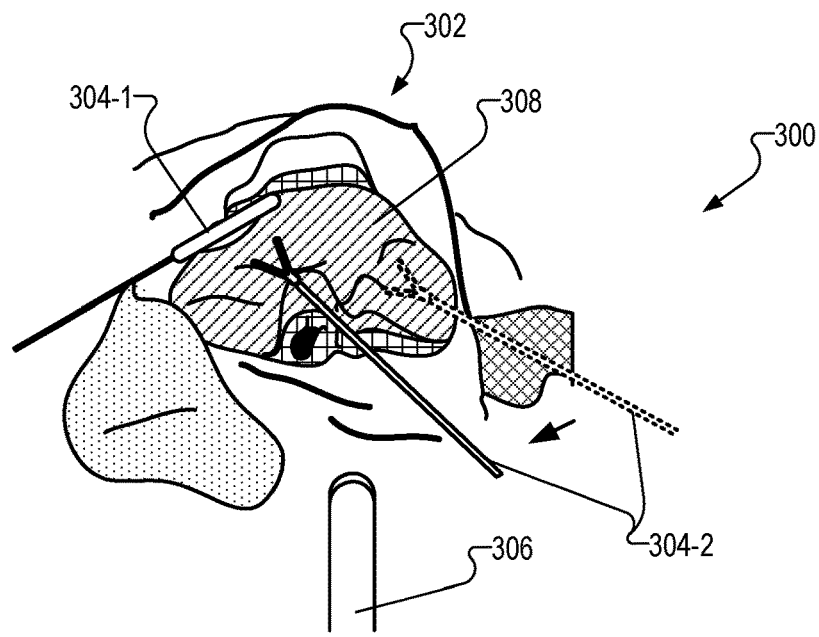
FIG. 6A illustrates an exemplary surgical area associated with a patient according to principles described herein.
Figure 6B:
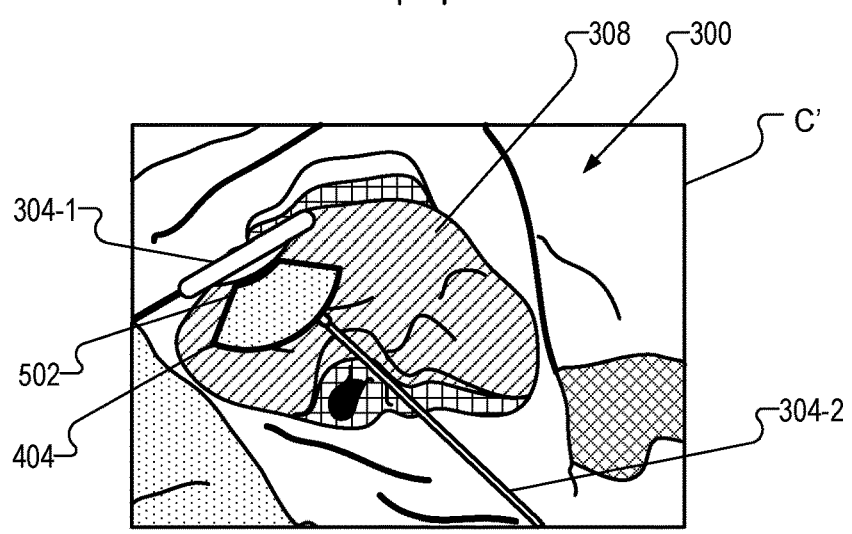
FIG. 6B illustrates an exemplary composite medical image displayed by a display device according to principles described herein.
Figure 6C:
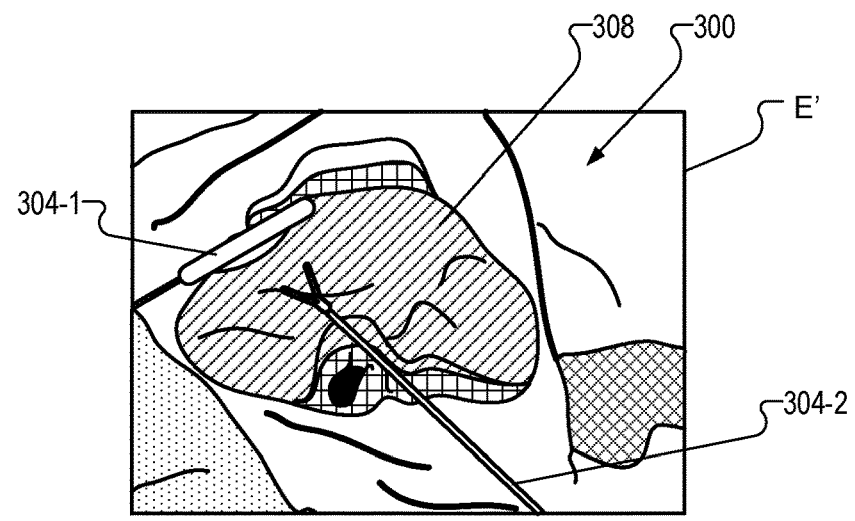
FIG. 6C illustrates an exemplary image of the surgical area of FIG. 6A displayed by a display device according to principles described herein.

FIGS. 6A and 6B illustrate an example of an overlap between at least a portion of augmentation region 502 and at least a portion of a view of an object located at surgical area 300. FIG. 6A is the same as FIG. 3A except that scissors 304-2 have been moved from their initial position (shown in broken lines in FIG. 6A) to a new position (shown in solid lines in FIG. 6A) closer to ultrasound probe 304-1. FIG. 6B illustrates an exemplary composite image C' generated after scissors 304-2 have moved to the new position. Composite image C' shows a view of surgical area 300 and augmentation region 502 that shows ultrasound image 404 generated by ultrasound probe 304-1. As shown in FIG. 6B, the distal end portion of scissors 304-2 overlaps with a portion of augmentation region 502 in composite image C'. System 100 is configured to detect the overlap between augmentation region 502 and scissors 304-2 and, in response, direct the display device to display only endoscopic image E', which shows the view of surgical area 300 as captured by imaging device 306. FIG. 6C illustrates an exemplary endoscopic image E' captured after scissors 304-2 have moved to the new position. As can be seen, augmentation region 502 has been removed so that the surgeon can easily see surface anatomy 308 at surgical area 300 and thus determine a position of scissors 304-2 relative to surface anatomy 308.

The manner in which system 100 may detect an overlap in a composite medical image between at least a portion of an augmentation region (e.g., augmentation region 206 or augmentation region 502 including 3D model 402 and/or ultrasound image 404) and a view of an object located at the surgical area will now be described. System 100 may detect an overlap in a composite medical image between at least a portion of an augmentation region and a view of an object in any suitable manner.

Figure 7A:
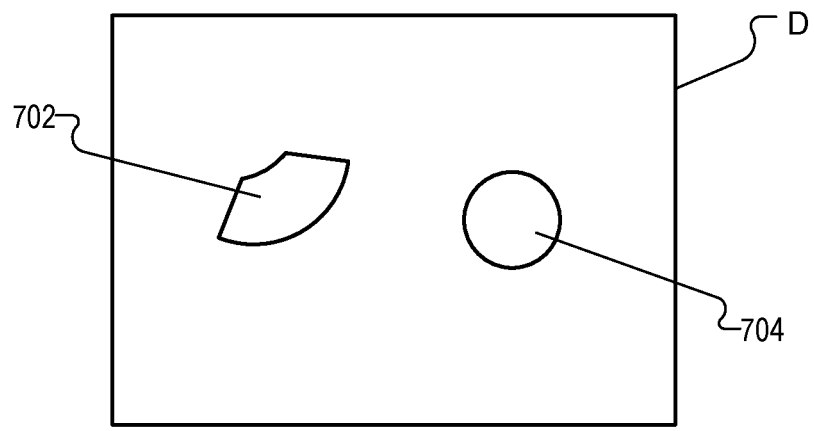
FIGS. 7A and 7B illustrate exemplary detection images for detecting an overlap according to principles described herein.

An exemplary manner of overlap detection based on position tracking will now be described with reference to FIGS. 7A and 7B. FIG. 7A illustrates an exemplary detection image D used in detecting an overlap. Detection image D includes an augmentation region representation 702 and an object representation 704. Augmentation region representation 702 represents an augmentation region in a composite medical image (e.g., augmentation region 206 in image 200 or augmentation region 502 in composite image C). Object representation 704 represents an object (e.g., scissors 304-2) located at a surgical area associated with a patient and is positioned within detection image D based on the location of the object in the surgical area. Generation of detection image D will be described below in more detail. In certain examples, overlap in the composite medical image between the augmentation region and the object may be detected when object representation 704 is detected to be in contact with augmentation region representation 702 in detection image D, as will be explained below in more detail.

FIG. 7A shows detection image D generated when the object (e.g., scissors 304-2) is located at an initial position. As shown, object representation 704 is not in contact with augmentation region representation 702 because no pixel of object representation 704 is adjacent to or overlapping with a pixel of augmentation region representation 702. Therefore, system 100 does not detect an overlap between the object and the augmentation region in the composite medical image (e.g., augmentation region 502 in composite image C).

Figure 7B:
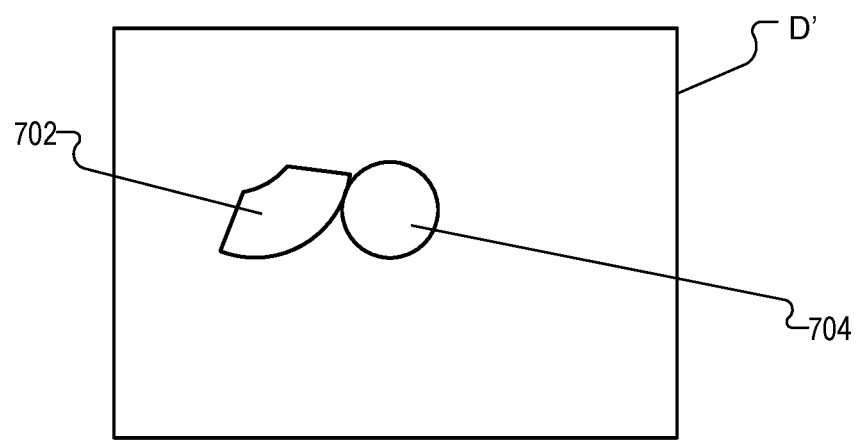

FIG. 7B shows an exemplary detection image D' generated after movement of the object to a new position in the surgical area. As shown, object representation 704 is in contact with augmentation region representation 702 because one or more pixels of object representation 704 is adjacent to or overlapping one or more pixels of augmentation region representation 702. In response to detecting that object representation 704 is in contact with augmentation region representation 702, system 100 determines that at least a portion of the augmentation region (e.g., augmentation region 502 in composite image C) is overlapped by the object.

In some embodiments, detection image D does not include augmentation region representation 702. Since detection image D is set to be the same size (I×J pixels) as mask image M, the window region (e.g., window region 412) in the mask image M represents the augmentation region (e.g., augmentation region 502) in the composite medical image. Therefore, overlap may be detected by comparing detection image D with mask image M to determine if object representation 704 in detection image D and the window region in mask image M (e.g., window region 412) have one or more pixel locations in common.

Generation of detection image D will now be described. In some examples detection image D is set to be the same size (I×J pixels) as mask image M. As mentioned, augmentation region representation 702 represents an augmentation region in a composite medical image. Accordingly, augmentation region representation 702 is formed in detection image D with the same size, shape, and position as the augmentation region in the composite medical image (e.g., augmentation region 206 in image 200 or augmentation region 502 in composite image C). Augmentation region representation 702 may be formed in detection image D in any suitable way. For example, mask image M may be inverted by setting pixels in mask region 410 to white and pixels in window region 412 to black. Alternatively, ultrasound image 404 and/or frame 406 may be projected onto detection image D, such as by virtual imaging device 408 capturing detection image D. That is, detection image D shows a view of ultrasound image 404 and/or frame 406 in virtual surgical area 400 as captured by virtual imaging device 408. As yet another example, augmentation region representation 702 may be formed in detection image D by using object recognition to detect a size, shape, and position of the augmentation region in the composite medical image.

As mentioned, object representation 704 represents an object located in the surgical area associated with the patient. Object representation 704 may be any size or shape as may suit a particular implementation. As shown in FIG. 7A, object representation 704 is circular and represents, for example, a distal end portion of a surgical instrument (e.g., scissors 304-2). Additionally, object representation 704 is larger than the distal end portion of the surgical instrument, thereby encompassing the entire area in which an end effector of the surgical instrument may move. In other examples object representation 704 is the same shape and size as the distal end portion of the surgical instrument. Adjusting the size and/or shape of object representation 704 will adjust the sensitivity with which system 100 detects an overlap between an augmentation region in a composite medical image and an object located in the surgical area. Accordingly, in some examples system 100 may be configured to receive user input to adjust the sensitivity of overlap detection, such as by adjusting the size and/or shape of object representation 704.

Object representation 704 may be formed in detection image D in any suitable way. In some examples object representation 704 is formed in detection image D by tracking the pose (e.g., position and/or orientation) of the corresponding object in the surgical area associated with the patient and projecting a view of the object (or a representation of the object) onto detection image D. For example, as mentioned above, the view of virtual surgical area 400 in virtual image V is registered with the view of surgical area 300 in endoscopic image E. Accordingly, the pose of scissors 304-2 may also be tracked in virtual surgical area 400. A 3D bounding volume representing a distal end portion of scissors 304-2 may then be generated in virtual surgical area 400 at the tracked location of the distal end portion of scissors 304-2. The 3D bounding volume representing scissors 304-2 may then be projected onto detection image D as object representation 704.

Figure 8:
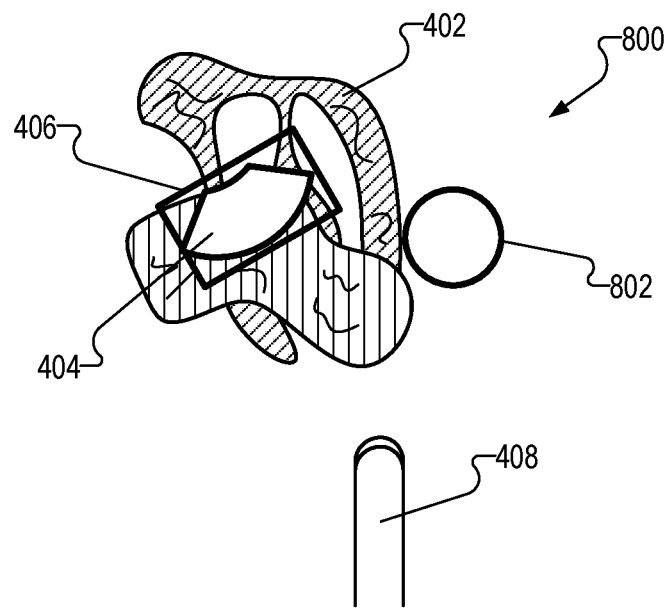
FIG. 8 illustrates a virtual surgical area according to principles described herein.

FIG. 8 illustrates an exemplary virtual surgical area 800 including a 3D bounding volume representing scissors 304-2 located in surgical area 300. FIG. 8 is the same as FIG. 4A except that virtual surgical area 800 includes a spherical bounding volume 802 generated around a distal end portion of scissors 304-2. FIG. 8 shows that virtual surgical area 800 includes ultrasound image 404 and frame 406, but these may be omitted from virtual surgical area 800 in some embodiments. Bounding volume 802 may be any shape and size as may suit a particular implementation. Because bounding volume 802 is projected onto detection image D as object representation 704, the shape and size of bounding volume 802 determines the shape and size of object representation 704. As shown in FIG. 8, bounding volume 802 is spherical and is sized to encompass at least the entire area in which the distal end portion of scissors 304-2 (e.g., the end effector of scissors 304-2) may move. In alternative embodiments bounding volume 802 may be the same shape and/or size as scissors 304-2. Once bounding volume 802 is generated in virtual surgical area 800, bounding volume 802 is projected onto detection image D as object representation 704. For example, virtual imaging device 408 may "capture," as detection image D, an image of virtual surgical area 800 showing a view of bounding volume 802 as object representation 704.

Object representation 704 may alternatively be formed in detection image D based on object recognition. For example, system 100 may be configured to analyze an image showing a view of the surgical area (e.g., endoscopic image E) to identify and recognize in the image an object located at the surgical area. System 100 may utilize any suitable image recognition technology to identify and recognize the object. When the object is detected, system 100 may generate object representation 704 in detection image D at a location corresponding to the location in the image of the surgical area where the object is detected.

In some examples the size and shape of object representation 704 is predefined based on the type of the object detected. To illustrate, system 100 may analyze endoscopic image E (see FIG. 3B) and detect scissors 304-2. System 100 may then access a lookup table to determine a shape (e.g., circular), size (e.g., radius of 100 pixels), and position (e.g., at the joint of the end effector) of object representation 704 for scissors 304-2.

In alternative examples the shape and size of object representation 704 is based on the size and shape of the detected object in the image. To illustrate, system 100 may analyze an image of a surgical area and detect a pool of blood. System 100 may then draw object representation 704 in detection image D to be the same shape and size as the detected pool of blood. In this way system 100 may be configured to detect when a view of excessive bleeding overlaps with augmentation region 502 in composite image C.

Forming object representation 704 based on object recognition is useful to detect an overlap with an object for which there may not be kinematic or positional information, such as a surgical mesh, a patch, a surgeon's finger or hand, and the like.

As mentioned, in response to detection of an overlap between at least a portion of an object with at least a portion of an augmentation region included in a composite medical image, system 100 is configured to adjust the image to decrease an extent of the occlusion over at least a portion of the view of the surgical area by the augmentation region. In some examples, the adjusting of the image is further conditioned on detecting that the object is in motion. In this example system 100 infers from the motion of the object (e.g., a surgical instrument) that the surgeon is intending to interact with patient tissue. However, if the object is stationary but the augmentation region is moving (e.g., the user is moving the augmentation region), system 100 infers from the lack of motion of the object that the surgeon is not intending to interact with patient tissue. Therefore, there is little risk of contact with the patient tissue by displaying the augmentation region. System 100 may determine that the object is in motion in any suitable way, such as based on kinematic information associated with the object, image recognition, sensors included in the object (e.g., surgical instrument sensors), and the like.

In some examples system 100 is configured to adjust the image only if the object is detected to be moving toward the augmentation region. Object motion toward the augmentation region may be detected in any suitable way. In some embodiments object motion toward augmentation region may be inferred by detecting object motion toward patient tissue since the augmentation region shows a view of subsurface anatomy beneath the patient tissue. To this end, a depth map may be generated from stereoscopic images of the surgical area, and movement of the object (e.g., a distal end of the surgical instrument) relative to the surface tissue may be determined based on the depth map and/or kinematic information associated with the object.

Additionally or alternatively to using a depth map, system 100 may determine that the object is moving toward the surface tissue if the object is detected to be moving away from the imaging device (e.g., imaging device 306). On the other hand, the object is moving away from the surface tissue (and thereby determined to be moving away from the augmentation region) if the object is moving toward the imaging device. Movement of the object away from or toward the imaging device may be detected in any suitable way, such as based on kinematic information associated with the object and the imaging device.

In some embodiments, system 100 may be configured to detect that overlap between an augmentation region and an object in a composite medical image has ended. In response, system 100 may adjust the image to turn on and/or increase an extent of occlusion, by the augmentation region, over the portion of the view of the surgical area. For instance, while the display device is displaying composite image E' (see FIG. 6C), system 100 may detect that scissors 304-2 have moved to another position such that object representation 704 in detection image does not contact augmentation region representation 702. Accordingly, system 100 may direct the display device to display another composite image C that shows a view of surgical area 300 and augmentation region 502, including ultrasound image 404 and/or 3D model 402. As another example, if the opacity of an augmentation region (e.g., augmentation region 502) has been decreased due to a detected overlap between the augmentation region and an object, system 100 may adjust the blending of images E, S, V, and M to increase the opacity of the augmentation region. In these ways system 100 may intelligently hide supplemental content only while a view of an object located at the surgical area would overlap with at least a portion of the augmentation region including the supplemental content.

In the foregoing description system 100 is configured to detect an overlap between an object located at a surgical area associated with a patient and at least a portion of an augmentation region included in composite medical image, the augmentation region showing a representation of subsurface anatomy. However, system 100 is not limited to detecting an overlap with a portion of an augmentation region showing subsurface anatomy, but may be configured to detect an overlap with an augmentation region showing any other type(s) of supplemental content.

In some implementations, system 100 may operate as part of or in conjunction with a computer-assisted surgical system. As such, an exemplary computer-assisted surgical system will now be described. The described exemplary computer-assisted surgical system is illustrative and not limiting. System 100 may operate as part of or in conjunction with the computer-assisted surgical system described herein and/or with other suitable computer-assisted surgical systems.

Figure 9:
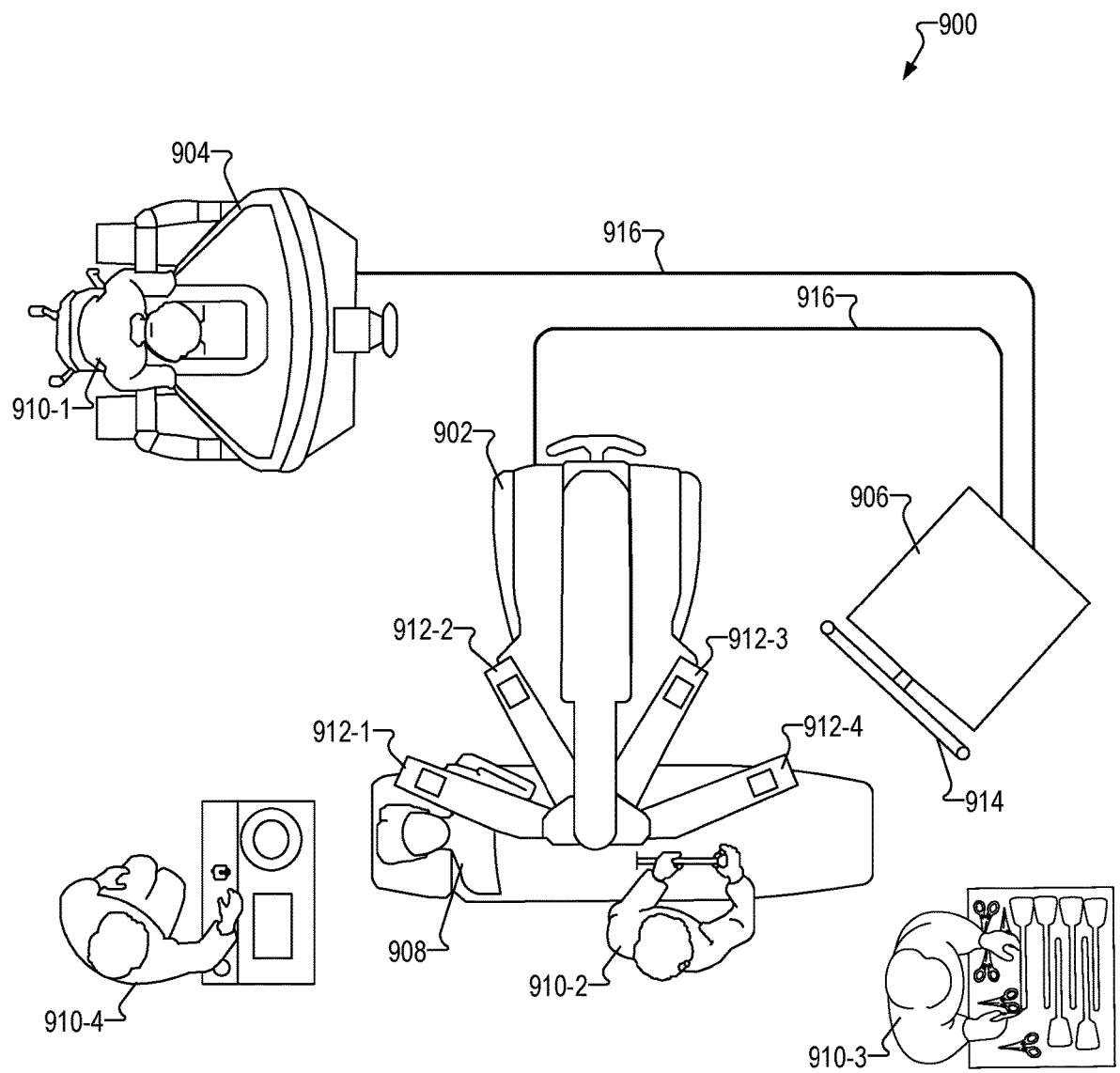
FIG. 9 illustrates an exemplary computer-assisted surgical system according to principles described herein.

FIG. 9 illustrates an exemplary computer-assisted surgical system 900 ("surgical system 900"). As described herein, system 100 may be implemented by surgical system 900, connected to surgical system 900, and/or otherwise used in conjunction with surgical system 900.

As shown, surgical system 900 may include a manipulating system 902, a user control system 904, and an auxiliary system 906 communicatively coupled one to another. Surgical system 900 may be utilized by a surgical team to perform a computer-assisted surgical procedure on a patient 908. As shown, the surgical team may include a surgeon 910-1, an assistant 910-2, a nurse 910-3, and an anesthesiologist 910-4, all of whom may be collectively referred to as "surgical team members 910." Additional or alternative surgical team members may be present during a surgical session as may serve a particular implementation.

While FIG. 9 illustrates an ongoing minimally invasive surgical procedure, it will be understood that surgical system 900 may similarly be used to perform open surgical procedures or other types of surgical procedures that may similarly benefit from the accuracy and convenience of surgical system 900. Additionally, it will be understood that the surgical session throughout which surgical system 900 may be employed may not only include an operative phase of a surgical procedure, as is illustrated in FIG. 9, but may also include preoperative, postoperative, and/or other suitable phases of the surgical procedure. A surgical procedure may include any procedure in which manual and/or instrumental techniques are used on a patient to investigate or treat a physical condition of the patient.

As shown in FIG. 9, manipulating system 902 may include a plurality of manipulator arms 912 (e.g., manipulator arms 912-1 through 912-4) to which a plurality of surgical instruments may be coupled. Each surgical instrument may be implemented by any suitable surgical tool (e.g., a tool having tissue-interaction functions), medical tool, imaging device (e.g., an endoscope), sensing instrument (e.g., a force-sensing surgical instrument), diagnostic instrument, or the like that may be used for a computer-assisted surgical procedure on patient 908 (e.g., by being at least partially inserted into patient 908 and manipulated to perform a computer-assisted surgical procedure on patient 908). While manipulating system 902 is depicted and described herein as including four manipulator arms 912, it will be recognized that manipulating system 902 may include only a single manipulator arm 912 or any other number of manipulator arms as may serve a particular implementation.

Manipulator arms 912 and/or surgical instruments attached to manipulator arms 912 may include one or more displacement transducers, orientational sensors, and/or positional sensors used to generate raw (i.e., uncorrected) kinematics information. One or more components of surgical system 900 may be configured to use the kinematics information to track (e.g., determine positions and orientations of) and/or control the surgical instruments.

User control system 904 may be configured to facilitate control by surgeon 910-1 of manipulator arms 912 and surgical instruments attached to manipulator arms 912. For example, surgeon 910-1 may interact with user control system 904 to remotely move or manipulate manipulator arms 912 and the surgical instruments. To this end, user control system 904 may provide surgeon 910-1 with images (e.g., high-definition 3D images, composite medical images, etc.) of a surgical area associated with patient 908 as captured by an imaging system (e.g., including any of the imaging devices described herein). In certain examples, user control system 904 may include a stereo viewer having two displays where stereoscopic images of a surgical area associated with patient 908 and generated by a stereoscopic imaging system may be viewed by surgeon 910-1. Surgeon 910-1 may utilize the images to perform one or more procedures with one or more surgical instruments attached to manipulator arms 912.

To facilitate control of surgical instruments, user control system 904 may include a set of master controls. These master controls may be manipulated by surgeon 910-1 to control movement of surgical instruments (e.g., by utilizing robotic and/or teleoperation technology). The master controls may be configured to detect a wide variety of hand, wrist, and finger movements by surgeon 910-1. In this manner, surgeon 910-1 may intuitively perform a procedure using one or more surgical instruments.

Auxiliary system 906 may include one or more computing devices configured to perform primary processing operations of surgical system 900. In such configurations, the one or more computing devices included in auxiliary system 906 may control and/or coordinate operations performed by various other components (e.g., manipulating system 902 and user control system 904) of surgical system 900. For example, a computing device included in user control system 904 may transmit instructions to manipulating system 902 by way of the one or more computing devices included in auxiliary system 906. As another example, auxiliary system 906 may receive, from manipulating system 902, and process image data representative of images captured by an imaging device attached to one of manipulator arms 912.

In some examples, auxiliary system 906 may be configured to present visual content to surgical team members 910 who may not have access to the images provided to surgeon 910-1 at user control system 904. To this end, auxiliary system 906 may include a display monitor 914 configured to display one or more user interfaces, such as images (e.g., 2D images, composite medical images, etc.) of the surgical area, information associated with patient 908 and/or the surgical procedure, and/or any other visual content as may serve a particular implementation. For example, display monitor 914 may display images of the surgical area together with additional content (e.g., graphical content, contextual information, etc.) concurrently displayed with the images. In some embodiments, display monitor 914 is implemented by a touchscreen display with which surgical team members 910 may interact (e.g., by way of touch gestures) to provide user input to surgical system 900.

Manipulating system 902, user control system 904, and auxiliary system 906 may be communicatively coupled one to another in any suitable manner. For example, as shown in FIG. 9, manipulating system 902, user control system 904, and auxiliary system 906 may be communicatively coupled by way of control lines 916, which may represent any wired or wireless communication link as may serve a particular implementation. To this end, manipulating system 902, user control system 904, and auxiliary system 906 may each include one or more wired or wireless communication interfaces, such as one or more local area network interfaces, Wi-Fi network interfaces, cellular interfaces, etc.

Figure 10:
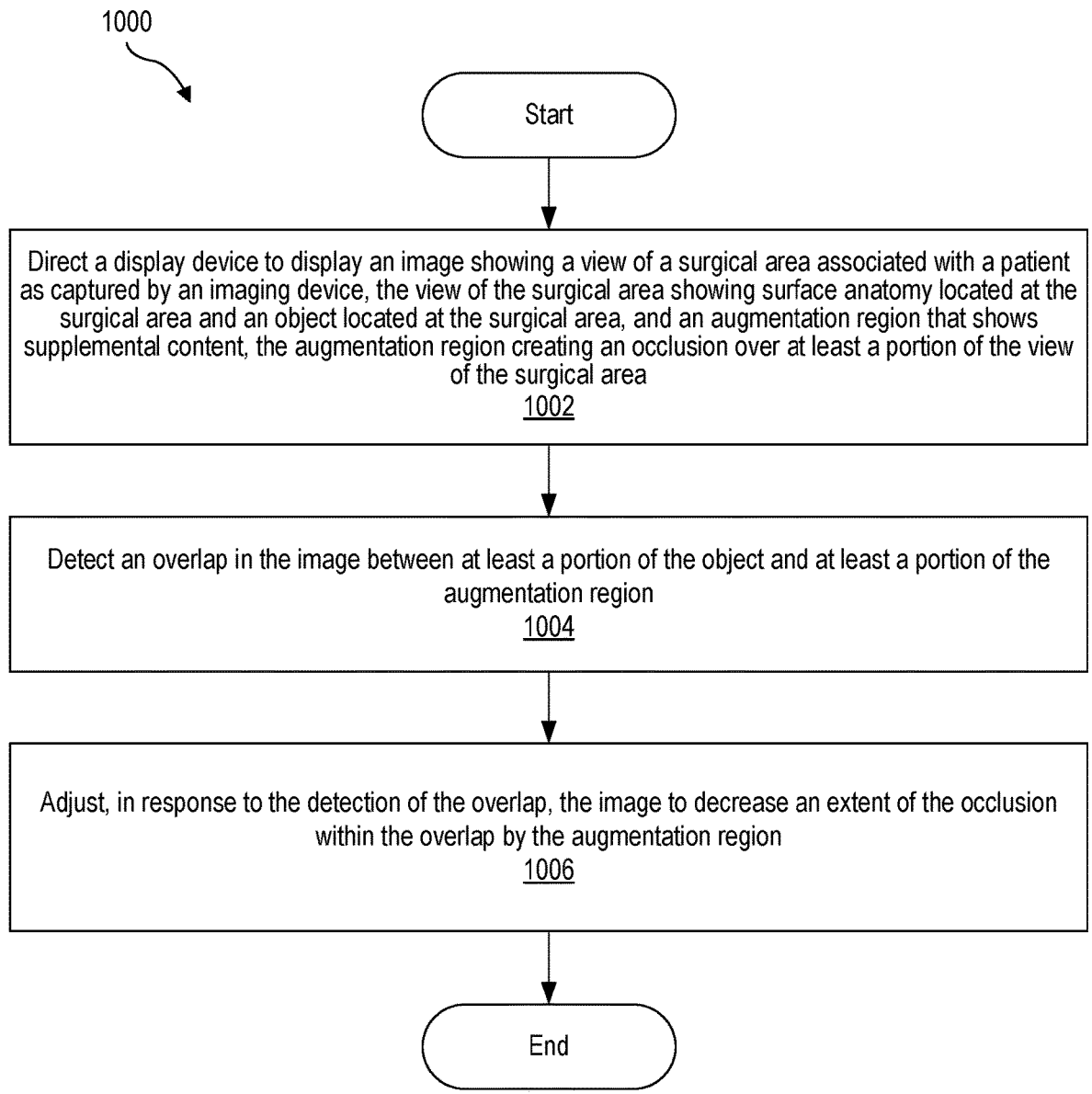
FIG. 10 illustrates an exemplary method according to principles described herein.

FIG. 10 shows an exemplary method 1000. While FIG. 10 illustrates exemplary operations according to one embodiment, other embodiments may omit, add to, reorder, combine, and/or modify any of the steps shown in FIG. 10 One or more of the operations shown in in FIG. 10 may be performed by system 100, any components included therein, and/or any implementation thereof.

In operation 1002, a composite medical imaging system directs a display device to display an image (e.g., composite medical image C) showing a view of a surgical area associated with a patient, as captured by an imaging device included in a computer-assisted surgical system, and an augmentation region. The view of the surgical area shows surface anatomy located at the surgical area and an object located at the surgical area, and the augmentation region shows supplemental content, the augmentation region creating an occlusion over at least a portion of the view of the surgical area. Operation 1002 may be performed in any of the ways described herein.

In operation 1004, the composite medical imaging system detects an overlap in the image between at least a portion of the object and at least a portion of the augmentation region. Operation 1004 may be performed in any of the ways described herein.

In operation 1006, the composite medical imaging system adjusts, in response to the detection of the overlap, the image to decrease an extent of the occlusion within the overlap by the augmentation region. Operation 1006 may be performed in any of the ways described herein.

In some examples, a non-transitory computer-readable medium storing computer-readable instructions may be provided in accordance with the principles described herein. The instructions, when executed by a processor of a computing device, may direct the processor and/or computing device to perform one or more operations, including one or more of the operations described herein. Such instructions may be stored and/or transmitted using any of a variety of known computer-readable media.

A non-transitory computer-readable medium as referred to herein may include any non-transitory storage medium that participates in providing data (e.g., instructions) that may be read and/or executed by a computing device (e.g., by a processor of a computing device). For example, a non-transitory computer-readable medium may include, but is not limited to, any combination of non-volatile storage media and/or volatile storage media. Exemplary non-volatile storage media include, but are not limited to, read-only memory, flash memory, a solid-state drive, a magnetic storage device (e.g. a hard disk, a floppy disk, magnetic tape, etc.), ferroelectric random-access memory ("RAM"), and an optical disc (e.g., a compact disc, a digital video disc, a Blu-ray disc, etc.). Exemplary volatile storage media include, but are not limited to, RAM (e.g., dynamic RAM).

Figure 11:
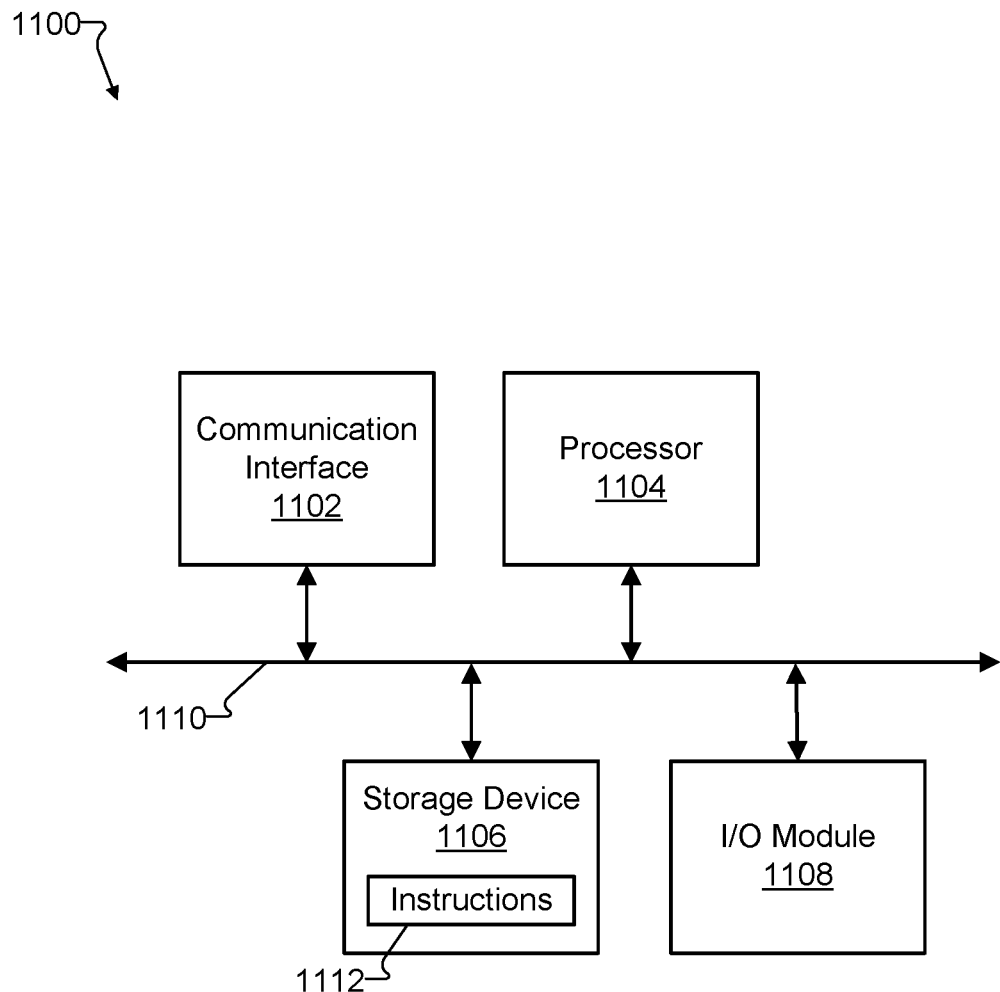
FIG. 11 illustrates an exemplary computing device according to principles described herein.

FIG. 11 illustrates an exemplary computing device 1100 that may be specifically configured to perform one or more of the processes described herein. Any of the systems, units, computing devices, and/or other components described herein may be implemented by computing device 1100.

As shown in FIG. 11, computing device 1100 may include a communication interface 1102, a processor 1104, a storage device 1106, and an input/output ("I/O") module 1108 communicatively connected one to another via a communication infrastructure 1110. While an exemplary computing device 1100 is shown in FIG. 11, the components illustrated in FIG. 11 are not intended to be limiting. Additional or alternative components may be used in other embodiments. Components of computing device 1100 shown in FIG. 11 will now be described in additional detail.

Communication interface 1102 may be configured to communicate with one or more computing devices. Examples of communication interface 1102 include, without limitation, a wired network interface (such as a network interface card), a wireless network interface (such as a wireless network interface card), a modem, an audio/video connection, and any other suitable interface.

Processor 1104 generally represents any type or form of processing unit capable of processing data and/or interpreting, executing, and/or directing execution of one or more of the instructions, processes, and/or operations described herein. Processor 1104 may perform operations by executing computer-executable instructions 1112 (e.g., an application, software, code, and/or other executable data instance) stored in storage device 1106.

Storage device 1106 may include one or more data storage media, devices, or configurations and may employ any type, form, and combination of data storage media and/or device. For example, storage device 1106 may include, but is not limited to, any combination of the non-volatile media and/or volatile media described herein. Electronic data, including data described herein, may be temporarily and/or permanently stored in storage device 1106. For example, data representative of computer-executable instructions 1112 configured to direct processor 1104 to perform any of the operations described herein may be stored within storage device 1106. In some examples, data may be arranged in one or more databases residing within storage device 1106.

I/O module 1108 may include one or more I/O modules configured to receive user input and provide user output. I/O module 1108 may include any hardware, firmware, software, or combination thereof supportive of input and output capabilities. For example, I/O module 1108 may include hardware and/or software for capturing user input, including, but not limited to, a keyboard or keypad, a touchscreen component (e.g., touchscreen display), a receiver (e.g., an RF or infrared receiver), motion sensors, and/or one or more input buttons.

I/O module 1108 may include one or more devices for presenting output to a user, including, but not limited to, a graphics engine, a display (e.g., a display screen), one or more output drivers (e.g., display drivers), one or more audio speakers, and one or more audio drivers. In certain embodiments, I/O module 1108 is configured to provide graphical data to a display for presentation to a user. The graphical data may be representative of one or more graphical user interfaces and/or any other graphical content as may serve a particular implementation.

In the preceding description, various exemplary embodiments have been described with reference to the accompanying drawings. It will, however, be evident that various modifications and changes may be made thereto, and additional embodiments may be implemented, without departing from the scope of the invention as set forth in the claims that follow. For example, certain features of one embodiment described herein may be combined with or substituted for features of another embodiment described herein. The description and drawings are accordingly to be regarded in an illustrative rather than a restrictive sense.

What is claimed is:

1. A system comprising:
a memory storing instructions; and
a processor communicatively coupled to the memory and configured to execute the instructions to:
direct a display device to display:
an image captured by an imaging device and showing a view of a surgical area associated with a patient, the view of the surgical area showing surface anatomy located at the surgical area and an object located at the surgical area, and
an augmentation region within the image and that shows supplemental content, the augmentation region creating an occlusion over at least a portion of the view of the surgical area;
detect an overlap in the image between at least a portion of the object and at least a portion of the augmentation region; and
adjust, in response to the detection of the overlap, the image to decrease an extent of the occlusion within the overlap by the augmentation region.

2. The system of claim 1, wherein the adjusting of the image to decrease the extent of the occlusion within the overlap by the augmentation region comprises removing the augmentation region from the image.

3. The system of claim 1, wherein the adjusting of the image to decrease the extent of the occlusion within the overlap by the augmentation region comprises decreasing an opacity of the augmentation region in the image.

4. The system of claim 1, wherein:
the processor is further configured to determine that the object is in motion, and
the adjusting of the image to decrease the extent of the occlusion within the overlap by the augmentation region is performed further in response to the determination that the object is in motion.

5. The system of claim 1, wherein the supplemental content comprises a representation of subsurface anatomy located beneath a portion of the surface anatomy that is within the occlusion created by the augmentation region.

6. The system of claim 5, wherein the representation of the subsurface anatomy comprises one or more of an ultrasound image of the subsurface anatomy, an image of a three-dimensional model of the subsurface anatomy, and a fluorescence image of the subsurface anatomy.

7. The system of claim 1, wherein the detection of the overlap comprises:
generating a detection image including an object representation that represents the object and an augmentation region representation that represents the augmentation region, and
determining that the object representation contacts the augmentation region representation.

8. A method comprising:
directing, by a composite medical imaging system, a display device to display:
an image captured by an imaging device and showing a view of a surgical area associated with a patient, the view of the surgical area showing surface anatomy located at the surgical area and an object located at the surgical area, and an augmentation region within the image and that shows supplemental content, the augmentation region creating an occlusion over at least a portion of the view of the surgical area;

detecting, by the composite medical imaging system, an overlap in the image between at least a portion of the object and at least a portion of the augmentation region; and adjusting, by the composite medical imaging system and in response to the detection of the overlap, the image to decrease an extent of the occlusion within the overlap by the augmentation region.

9. The method of claim 8, wherein the adjusting of the image to decrease the extent of the occlusion within the overlap by the augmentation region comprises removing the augmentation region from the image.

10. The method of claim 8, wherein the adjusting of the image to decrease the extent of the occlusion within the overlap by the augmentation region comprises decreasing an opacity of the augmentation region in the image.

11. The method of claim 8, further comprising:
determining that the object is in motion,
wherein the adjusting of the image to decrease the extent of the occlusion within the overlap by the augmentation region is performed further in response to the determination that the object is in motion.

12. The method of claim 8, wherein the supplemental content comprises a representation of subsurface anatomy located beneath a portion of the surface anatomy that is within the occlusion created by the augmentation region.

13. The method of claim 12, wherein the representation of the subsurface anatomy comprises one or more of an ultrasound image of the subsurface anatomy, an image of a three-dimensional model of the subsurface anatomy, and a fluorescence image of the subsurface anatomy.

14. The method of claim 8, wherein the detecting of the overlap comprises:
generating a detection image including an object representation that represents the object and an augmentation region representation that represents the augmentation region, and
determining that the object representation contacts the augmentation region representation.

15. A non-transitory computer-readable medium storing instructions that, when executed, direct at least one processor of a computing device to:

direct a display device to display:
an image captured by an imaging device and showing a view of a surgical area associated with a patient, the view of the surgical area showing surface anatomy located at the surgical area and an object located at the surgical area, and
an augmentation region within the image and that shows supplemental content, the augmentation region creating an occlusion over at least a portion of the view of the surgical area;

detect an overlap in the image between at least a portion of the object and at least a portion of the augmentation region; and adjust, in response to the detection of the overlap, the image to decrease an extent of the occlusion within the overlap by the augmentation region.

16. The non-transitory computer-readable medium of claim 15, wherein the adjusting of the image to decrease the extent of the occlusion within the overlap by the augmentation region comprises removing the augmentation region from the image.

17. The non-transitory computer-readable medium of claim 15, wherein the adjusting of the image to decrease the extent of the occlusion within the overlap by the augmentation region comprises decreasing an opacity of the augmentation region in the image.

18. The non-transitory computer-readable medium of claim 15, further storing instructions that, when executed, direct the at least one processor of the computing device to:
determine that the object is in motion,
wherein the adjusting of the image to decrease the extent of the occlusion within the overlap by the augmentation region is performed further in response to the determination that the object is in motion.

19. The non-transitory computer-readable medium of claim 15, wherein the supplemental content comprises a representation of subsurface anatomy located beneath a portion of the surface anatomy that is within the occlusion created by the augmentation region.

20. The non-transitory computer-readable medium of claim 19, wherein the representation of the subsurface anatomy comprises one or more of an ultrasound image of the subsurface anatomy, a three-dimensional model of the subsurface anatomy, and a fluorescence image of the subsurface anatomy.

* * * * *